Figure 1:
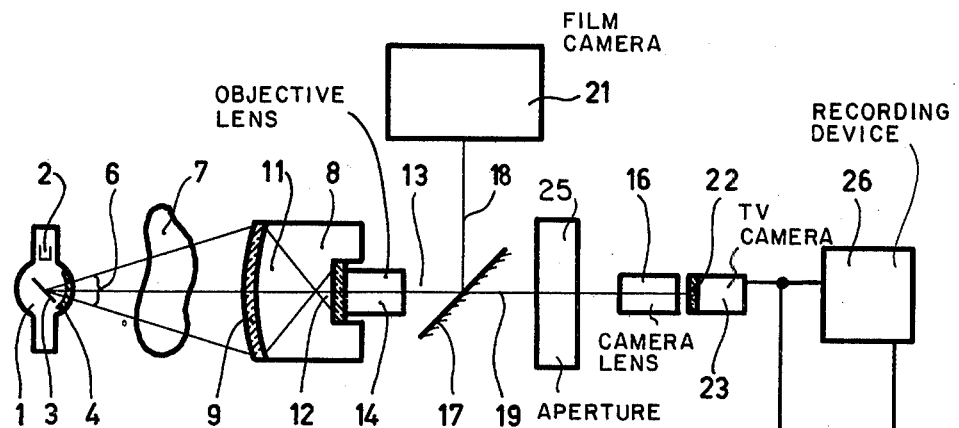

United States Patent [19]

Monte

[11] 4,085,328
[45] Apr. 18, 1978

[54] X-RAY EXAMINING DEVICE

[75] Inventor: George Leendert Adriaan Monte, Eindhoven, Netherlands

[73] Assignee: U.S. Philips Corporation, New York, N.Y.

[21] Appl. No.: 733,203

[22] Filed: Oct. 18, 1976

[30] Foreign Application Priority Data

Oct. 20, 1975 Netherlands .................. 7512256

[51] Int. Cl.² .............................................. G21K 1/04
[52] U.S. Cl. ............................ 250/416 TV; 250/512; 250/513
[58] Field of Search ............... 250/416 TV, 512, 513, 250/229

[56] References Cited

U.S. PATENT DOCUMENTS

| 3,121,798 | 2/1964 | Ploke | 250/229 |
| 3,448,270 | 6/1969 | Peyser | 250/513 |
| 3,912,936 | 10/1975 | Cunninghame et al. | 250/512 |
| 3,936,647 | 2/1976 | Fekete | 250/512 |

Primary Examiner—Archie R. Borchelt
Attorney, Agent, or Firm—Frank R. Trifari; Jack E. Haken

[57] ABSTRACT

An X-ray examining device comprises an optical aperture including adjustable sector-like laminations. The laminations are rotatable about axes perpendicular to the optical axis. The edges of the laminations are adapted to the optical system so that proper imaging is maintained in the case of a comparatively small opening of the aperture.

4 Claims, 3 Drawing Figures

X-RAY EXAMINING DEVICE

The invention relates to an X-ray examining device, comprising a radiation source, an X-ray image intensifier tube, an optical system, a recording device and a beam stopping aperture which is arranged between the image intensifier and the recording device.

In known devices of this kind, use is often made of an iris aperture which controls the luminous flux admitted to a recording device in the form of a television camera tube. The generally non-linear action of such an aperture is a drawback. Moreover, when a comparatively small aperture is used, image formation is disturbed. In modern X-ray examining apparatus, moreover, increasingly severe requirements for setting speed of the aperture are imposed. It is increasingly difficult for prior art apertures to satisfy these more stringent requirements.

The invention has for its object to provide an X-ray examining device comprising an aperture which allows, fast luminous flux control and in which the said drawbacks are eliminated while maintaining a small dimension measured in the direction of the beam path. An X-ray examining device in accordance with the invention comprises an aperture having a number of sector-like elements which are rotatable about axes which are oriented substantially perpendicularly to the optical axis.

By rotation of the sector-like elements, starting from a closed condition, a star-shaped passage for the image beam is produced. By a suitable choice of the shape of mutually adjoining ends of the laminations, it is possible to choose the shape of the passage and the variation thereof as a function of the rotation of the laminations. Moreover, the shape of the laminations can be adapted to the shape of adjoining optical elements of the image-forming device.

Some preferred embodiments in accordance with the invention will be described in detail hereinafter with reference to the diagrammatic drawing.

Figure 2:
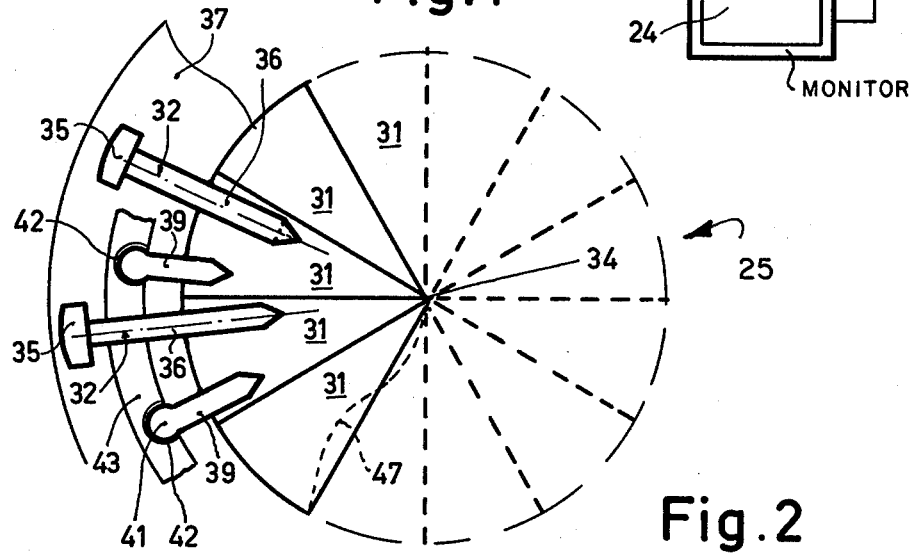
Figure 3:
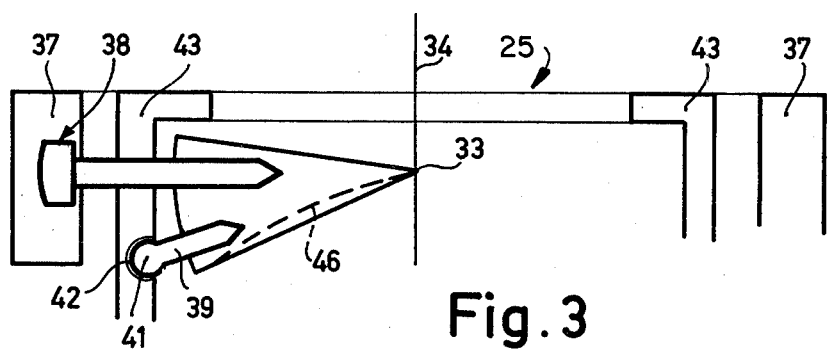

FIG. 1 is a diagrammatic view of an X-ray examining device in accordance with the invention, and FIGS. 2 and 3 are diagrammatic views of a preferred embodiment of an aperture in accordance with the invention, viewed in two different directions.

FIG. 1 shows an X-ray source 1, a cathode 2, an anode 3 and a radiation window 4 of an X-ray examining device. An object 7 is irradiated by an X-ray beam 6 and an X-ray shadow image is projected on an X-ray image intensifier tube 8. The X-ray beam to be used for the image formation is intercepted in an entrance screen 9 in the image intensifier tube and is converted into an electron beam 11 which is converted into a radiation beam 13 whose wavelength is preferably situated in or near the visible spectral range in an exit screen 12. In this case the exit window is coupled to an optical system which comprises a first lens system 14, also referred to as the basic objective, and a second lens system 16, also referred to an camera lens, wherebetween a semi-transparent or at least partly transparent mirror 17 is arranged. The mirror 17 splits the light beam 13 into two sub-beams 18 and 19. The part 18 is applied, for example, to a film or cassette camera 21 for recording images. The part 19 is applied to a target 22 of a television camera tube 23. A signal derived from the television camera tube can be displayed for direct visual observation on a monitor 24 or can be applied, for example, to a magnetic recording device 26 for electronic reading out. The image recorded in the form of a television signal can also be displayed on the monitor.

Between the semi-transparent mirror and the television camera tube there is arranged an aperture 25 whereby the luminous flux to the camera tube can be controlled between comparatively wide limits. For imaging it is advantageous to minimize the dimension of this aperture in the direction of the beam, otherwise an additional vignetting effect occurs in the image-formation. Use is often made of an automatically adjustable iris aperture which is adjusted for a large passage opening during fluroscopy for visual observation, where use is made of a comparatively small X-ray beam energy, while during the exposure, during which a comparatively high X-ray beam energy is used for a brief period of time, an automatic change-over to a small passage opening takes place and vice versa.

FIGS. 2 and 3 are an aperture 25 in accordance with the invention which consists of sector-like laminations 31. Each of these, for example, twelve laminations, is connected to a rotary shaft 32 so that the lamination can be rotated. The rotary shafts have a common point 33 which is situated on the optical axis 34 of the imaging system, all rotary shafts being directed perpendicular to the optical axis 34. In the closed condition, shown in FIG. 2, the aperture is fully closed. This closed condition may be obtained with more certainty by making the laminations overlap. On the other hand, minimal passage may be obtained in the closed condition by providing cut-outs in the laminations. The laminations are opened and closed by cams 35 which form the ends of drive shafts 36 which are rigidly connected to the laminations. FIG. 3 shows a lamination in the open condition, viewed in a direction transverse to the optical axis 34. The drive can be realized, for example, by means of a ring 37 which is connected to the cams by way of a screw connection 38. In order to keep the laminations in position during rotation, use is preferably made of guide cams 39 which are also rigidly connected to the laminations and which comprise a convex end 41 which is guided through a slot 42 provided in a ring 43. In an embodiment which is adapted to the X-ray examining device, the cams 35 are driven by means of an electric motor whereby the aperture can be simply, automatically adjusted as in known embodiments.

In the open condition the plane of the lamination is directed parallel to the optical axis. In a preferred embodiment, the edges of the laminations which face an adjoining lens of the system are adapted to the shape, (i.e. the radius of curvature) of the lens so that they are concave. This is denoted by a broken line 46 in FIG. 3.

In a further preferred embodiment, the limits of the laminations are shaped as indicated in FIG. 2 by a broken line 47. The limit of the lamination is chosen so that the shielding of the light beam in radial zones is as advantageous as possible for the image formation.

What is claimed is:

1. In an X-ray examining device comprising an X-ray source; an X-ray image intensifier tube disposed to receive radiation from said source which functions to produce optical image radiation in response thereto; optical system means, having an optical axis, for conducting said image radiation to recording means and a beam stopping aperture disposed about said optical axis between said intensifier tube and said recording means; the improvement wherein said aperture comprises a plurality of sector-like laminations, symmetrically disposed about said optical axis, each of said laminations being rotatable about separate axes which intersect said optical axis in a direction perpendicular thereto.

2. The device of claim 1 wherein the edges of said laminations are shaped in a non-linear curve so that functional relationship between luminous flux transmission through said aperture and the rotational position of said laminations varies with distance from said optical axis.

3. A device as claimed in claim 1 wherein said optical system means includes a lens disposed adjacent said aperture and wherein the shape of the edges of said laminations conform to the radius of curvature of said lens.

4. A device as claimed in claim 1 further including means for automatically controlling the adjustment of said aperture by rotating said laminations about their axes.

* * * * *